US009595116B2

(12) United States Patent
Kawamura

(10) Patent No.: US 9,595,116 B2
(45) Date of Patent: *Mar. 14, 2017

(54) BODY MOTION DETECTION DEVICE AND METHOD

(71) Applicant: FUJIFILM Corporation, Tokyo (JP)

(72) Inventor: Takahiro Kawamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/843,061

(22) Filed: Sep. 2, 2015

(65) Prior Publication Data
US 2015/0379726 A1 Dec. 31, 2015

Related U.S. Application Data

(63) Continuation of application No. PCT/JP2014/001095, filed on Feb. 28, 2014.

(30) Foreign Application Priority Data

Mar. 6, 2013 (JP) .................................. 2013-043672

(51) Int. Cl.
G06T 7/20 (2006.01)
A61B 6/00 (2006.01)
(Continued)

(52) U.S. Cl.
CPC .............. *G06T 7/20* (2013.01); *A61B 6/5264* (2013.01); *G06K 9/4604* (2013.01);
(Continued)

(58) Field of Classification Search
CPC .... G06T 7/20; G06T 5/20; G06T 5/40; G06T 7/2066; G06T 2207/10116; A61B 6/5264; G06K 9/4604; G06K 9/6298
(Continued)

(56) References Cited

U.S. PATENT DOCUMENTS 7,899,229 B2   3/2011  Luo et al.
2002/0181797 A1*  12/2002  Young ................... G06T 5/004
                                                            382/260
(Continued)

FOREIGN PATENT DOCUMENTS

JP         7-72253 A    3/1995
JP       8-266529 A   10/1996
(Continued)

OTHER PUBLICATIONS

U.S. Appl. No. 14/666,468, filed Mar. 24, 2015.
(Continued)

Primary Examiner — Amandeep Saini
(74) Attorney, Agent, or Firm — Birch, Stewart, Kolasch & Birch, LLP

(57) ABSTRACT

A contrast calculating unit calculates, as each of a contrast of a high frequency component and a contrast of a low frequency component of a transformed radiographic image, a contrast in a gradient direction of an edge portion in an analysis region with each of analysis points set by an analysis point setting unit being the center of the analysis region. A ratio calculating unit calculates, for each gradient direction, a ratio of the contrast of the high frequency component to the contrast of the low frequency component. A determining unit determines the smallest ratio as an index indicating the body motion, and determines whether or not there is a body motion during an imaging operation to take the radiographic image based on a result of statistical processing of the indexes at the analysis points. A display control unit displays a result of the determination on a display unit.

12 Claims, 7 Drawing Sheets

(51) Int. Cl.
*G06K 9/46* (2006.01)
*G06K 9/62* (2006.01)
*G06T 5/20* (2006.01)
*G06T 5/40* (2006.01)

(52) U.S. Cl.
CPC .............. *G06K 9/6298* (2013.01); *G06T 5/20* (2013.01); *G06T 5/40* (2013.01); *G06T 7/2066* (2013.01); *G06T 2207/10116* (2013.01)

(58) Field of Classification Search
USPC ........................................................ 382/103
See application file for complete search history.

(56) References Cited

U.S. PATENT DOCUMENTS

2012/0059239 A1 3/2012 Yamaguchi
2013/0121556 A1 5/2013 Matsumoto

FOREIGN PATENT DOCUMENTS

| | | |
|---|---|---|
| JP | 9-24039 A | 1/1997 |
| JP | 2008-220414 A | 9/2008 |
| JP | 2010-206067 A | 9/2010 |
| JP | 2012-75862 A | 4/2012 |
| JP | 2013-102850 A | 5/2013 |

OTHER PUBLICATIONS

International Search Report, issued in PCT/JP2014/001095, dated Jun. 17, 2014.
Luo et al., "Motion blur detection in radiographs", Proc. of SPIE, 2008, vol. 6914, No. 69140U, pp. 69140U-1-69140U-8.
Written Opinion of the International Searching Authority, issued in PCT/JP2014/001095, dated Jun. 17, 2014, with partial translation.

* cited by examiner

BODY MOTION DETECTION DEVICE AND METHOD

CROSS-REFERENCE TO RELATED APPLICATIONS

This application is a Continuation of PCT International Application No. PCT/JP2014/001095 filed on Feb. 28, 2014, which claims priority under 35 U.S.C. §119(a) to Japanese Patent Application No. 2013-043672 filed on Mar. 6, 2013. Each of the above applications is hereby expressly incorporated by reference, in its entirety, into the present application.

BACKGROUND

The present disclosure relates to a body motion detection device and a body motion detection method for detecting a body motion of a subject during an imaging operation using a radiographic image.

When a radiographic image of a subject is obtained by imaging the subject by applying radiation, such as an x-ray, to the subject, the obtained radiographic image may be blurred and the image quality may be degraded due to a body motion of the subject during the imaging operation. In particular, when the imaged body part is the neck, the chest, the abdomen, the lumbar, etc., which requires a long exposure time, or the subject is a child, the rate of occurrence of body motion is relatively high, and degradation of the obtained radiographic image is a problem.

The technologist who carries out an imaging operation can determine whether or not there is a body motion of the subject by observing the subject during the imaging operation and immediately checking the obtained radiographic image. However, since a monitor provided in the imaging room has low resolution and a reduced image of the radiographic image is displayed on the monitor, and the observation environment is often relatively bright, it is difficult to determine whether or not there is a body motion by observing the displayed radiographic image. In such a situation, one may consider enlarging the radiographic image; however, the operation to enlarge the radiographic image decreases the efficiency of the workflow of the technologist.

In order to address this problem, techniques to automatically detect a body motion based on a radiographic image have been proposed. For example, a technique involving learning degradation of edges contained in radiographic images as feature quantities in two directions, the vertical direction and the horizontal direction, extracting an edge from a radiographic image, and determining whether or not the radiographic image is blurred due to a body motion based on the learned feature quantities and the extracted edge has been proposed (see U.S. Pat. No. 7,899,229, hereinafter Patent Literature 1). Also, a technique involving learning feature points with respect to a specific body part, which is a side of the head, and detecting a body motion in an obtained radiographic image using the results of the learning has been proposed (see H. Luo et al., "Motion blur detection in radiographs", Proc. of SPIE, Vol. 6914, No. 69140U, pp. 69140U-1-69140U-8, 2008, hereinafter Non-Patent Literature 1).

SUMMARY

However, the techniques taught in Patent Literature 1 and Non-Patent Literature 1, which use the results of learning about a specific body part, are not applicable to a radiographic image of a body part for which the learning has not been performed. Further, the technique taught in Patent Literature 1, where degradation of an edge is learned as feature points in two directions, cannot achieve accurate body motion detection from a radiographic image that is obtained under imaging conditions different from those of the radiographic images used for the learning, or a radiographic image that contains a subject different from the subject contained in the radiographic images used for the learning, and has problems of low stability of detection and a narrow range of subjects to which the technique is applicable.

In view of the above-described circumstances, the present disclosure is directed to allowing accurate detection of a body motion contained in a radiographic image regardless of imaging conditions and the subject.

A body motion detection device according to the disclosure comprises: contrast calculating means for calculating a contrast of a high frequency component and a contrast of a low frequency component of a radiographic image at each of a plurality of analysis points contained in the radiographic image, the analysis points being set for calculation of the contrast of the high frequency component and the contrast of the low frequency component, wherein the contrast calculating means generates, from the radiographic image, a high frequency image containing the high frequency component and a low frequency image containing the low frequency component, determines, at each analysis point on each of the high frequency image and the low frequency image, a gradient direction of an edge portion contained in an analysis region with the analysis point being the center, and calculates a contrast along the gradient direction of each of the high frequency image and the low frequency image as the contrast of the high frequency component and the contrast of the low frequency component; ratio calculating means for calculating a ratio of the contrast of the high frequency component to the contrast of the low frequency component for the gradient direction determined at each of the analysis points; and determining means for determining the smallest ratio among the ratios calculated for the gradient directions as an index value indicating the body motion, and determining whether or not there is a body motion of a subject contained in the radiographic image based on a result of statistical processing of the index values at the analysis points.

In the body motion detection device according to the disclosure, the determining means may determine whether or not there is a body motion at analysis points with relatively low index values based on a statistic value, such as an average value, of the index values at the analysis points with the relatively low index values.

In the body motion detection device according to the disclosure, the determining means may generate a distribution of all the index values, and may determine whether or not there is a body motion based on a distribution of relatively low index values in the distribution of all the index values.

The determining means may determine, depending on a body part of the subject, whether or not to perform the determination as to whether or not there is a body motion based on the result of the statistical processing.

The body motion detection device according to the disclosure may further comprise analysis point setting means for setting the analysis point on the radiographic image.

In this case, the analysis point setting means may extract a region of the subject from the radiographic image, and may extract a point at which the low frequency component in the region exceeds a specific threshold value as the analysis point.

In the body motion detection device according to the disclosure, the analysis point setting means may set the analysis points in a region other than an inappropriate region which is inappropriate for the determination as to whether or not there is a body motion.

In this case, the inappropriate region may be at least one of an artificial object, gas, and a peripheral region of the subject contained in the radiographic image.

Alternatively or in addition, the analysis point setting means may set the inappropriate region depending on a body part of the subject and/or a purpose of diagnosis.

The description "sets the analysis points in a region other than an inappropriate region" may refer to either of detecting an inappropriate region and then setting the analysis points in a region other than the inappropriate region in the radiographic image, or setting the analysis points on the radiographic image and then removing an analysis point that is set in the inappropriate region.

The body motion detection device according to the disclosure may further comprise display control means for displaying a result of the determination as to whether or not there is a body motion on display means.

In particular, in the case where the analysis points are set, the display control means may display the radiographic image wherein information indicating a magnitude of the index value at each analysis point is added to the analysis point.

A body motion detection method according to the disclosure comprises: calculating a contrast of a high frequency component and a contrast of a low frequency component of a radiographic image at each of a plurality of analysis points contained in the radiographic image, the analysis points being set for calculation of the contrast of the high frequency component and the contrast of the low frequency component, wherein the contrast of the high frequency component and the contrast of the low frequency component are calculated by generating, from the radiographic image, a high frequency image containing the high frequency component and a low frequency image containing the low frequency component, determining, at each analysis point on each of the high frequency image and the low frequency image, a gradient direction of an edge portion contained in an analysis region with the analysis point being the center, and calculating a contrast along the gradient direction of each of the high frequency image and the low frequency image as the contrast of the high frequency component and the contrast of the low frequency component;

calculating a ratio of the contrast of the high frequency component to the contrast of the low frequency component for the gradient direction determined at each of the analysis points; and determining the smallest ratio among the ratios calculated for the gradient directions as an index value indicating the body motion, and determining whether or not there is a body motion of a subject contained in the radiographic image based on a result of statistical processing of the index values at the analysis points.

It should be noted that the disclosure may be provided in the form of a program for causing a computer to carry out the body motion detection method according to the disclosure.

According to the body motion detection device and method of the disclosure, a contrast of a high frequency component and a contrast of a low frequency component of a radiographic image are calculated, and a ratio of the contrast of the high frequency component to the contrast of the low frequency component is calculated. Based on this ratio, whether or not there is a body motion of a subject contained in the radiographic image is determined. When there is a body motion during an imaging operation, the contrast of the high frequency component in the obtained radiographic image decreases, whereas the contrast of the low frequency component in the radiographic image scarcely decreases. Further, while the contrast of the entire radiographic image varies depending on imaging conditions or the type of subject, the variation appears as a difference of the contrast of the low frequency component. Therefore, the ratio of the contrast of the high frequency component to the contrast of the low frequency component can be used as an index indicating whether or not there is a body motion. The disclosure does not uses results of learning, but uses the contrast of the high frequency component and the contrast of the low frequency component, which are independent from the imaging conditions or the type of subject, and thus allows stable determination as to whether or not there is a body motion without being influenced by the imaging conditions or the type of subject.

The body motion includes those due to movement of the subject as a whole, and those due to a local movement of the subject, such as respiration or heart beats. The local movement and the other type of movement have different statistic values or different statistic distributions of the index values. Determining whether or not there is a body motion based on a result of statistical processing of the index values at the analysis points allows detecting a local body motion.

In some cases, the subject may include an artificial object, such as a metal forming an artificial joint. Also, the radiographic image may contain an artificial object such as a lead protector when a lead protector is used during an imaging operation to protect the reproductive organs, or the like. Further, the digestive organs, such as the stomach and intestines, of the subject may include gas such as air. The shapes of such regions and the presence or absence of these regions in the subject vary among individuals, similarly to the skin line of the subject. Further, sharpness of edges of these regions is not so high, and, if the analysis points are set in these regions or on the skin line, it is difficult to accurately determine whether or not there is a body motion based on the ratio of the contrast of the high frequency component to the contrast of the low frequency component. Setting the analysis points in a region other than the inappropriate region, which is inappropriate for the determination as to whether or not there is a body motion, allows excluding the inappropriate region when the analysis points are set, thereby allowing accurately detecting whether or not there is a body motion.

DETAILED DESCRIPTION OF THE PREFERRED EMBODIMENTS

Figure 1:
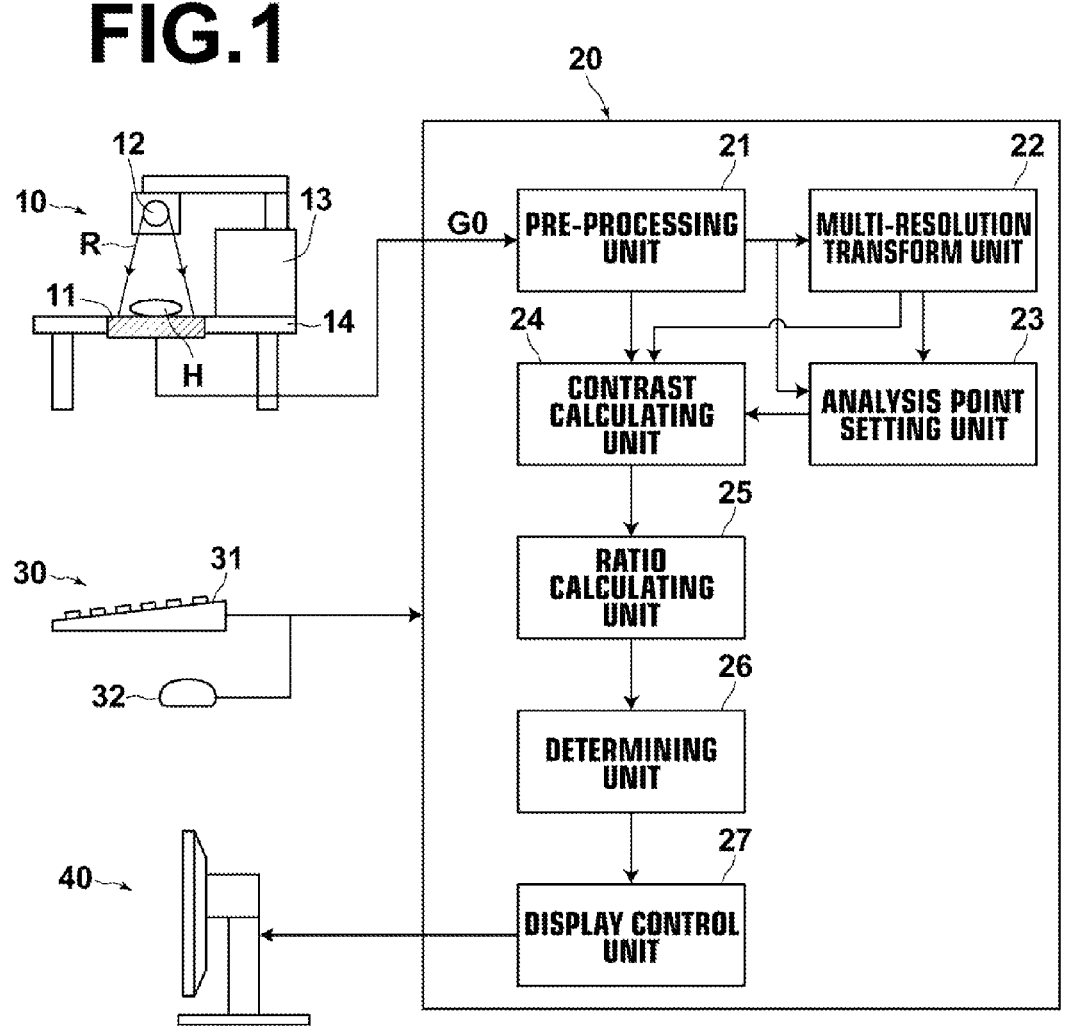
FIG. 1 is a diagram illustrating the schematic configuration of a radiographic imaging system to which a body motion detection device according to an embodiment of the disclosure are applied.

Hereinafter, an embodiment of the present disclosure will be described in detail with reference to the drawings. FIG. 1 is a diagram illustrating the schematic configuration of a radiographic imaging system to which a body motion detection device according to an embodiment of the disclosure is applied. The radiographic imaging system of this embodiment includes: an imaging apparatus 10 that images a subject to obtain a radiographic image G0 of the subject; a signal processing unit 20 that includes the body motion detection device of this embodiment and detects a body motion based on the radiographic image G0; an input unit 30 used to input various instructions to the signal processing unit 20; and a display unit 40 that displays the radiographic image obtained by imaging, etc.

The imaging apparatus 10 includes: a radiation-emitting tube 12 that applies radiation R to a subject H; an imaging control unit 13 that controls activation of the radiation-emitting tube 12; and an imaging table 14 on which the subject H is placed. The imaging table 14 includes a radiation detector 11 that outputs a radiation detection signal about the subject H. The radiation detection signal outputted by the radiation detector 11 corresponds to an energy level of the applied radiation for each of pixels arranged in a matrix. The detection signal is A/D converted and outputted as a digital image signal representing the radiographic image G0 of the subject H.

The radiation detector 11 may be one formed by a scintillator that emits visible light when exposed to radiation and a solid-state optical detection element that detects the visible light, which are stacked one on the other, as taught in Japanese Unexamined Patent Publication No. 7(1995)-072253, for example, or may be one including a radiation photoconductive layer that outputs an electric signal corresponding to energy of radiation when it is exposed to the radiation, as taught in Japanese Unexamined Patent Publication No. 2010-206067, for example.

The signal processing unit 20 includes: a pre-processing unit 21 to which the digital image signal representing the radiographic image G0 is inputted; a multi-resolution transform unit 22; an analysis point setting unit 23; a contrast calculating unit 24; a ratio calculating unit 25; a determining unit 26; and a display control unit 27. It should be noted that the contrast calculating unit 24, the ratio calculating unit 25, the determining unit 26, and the display control unit 27 forms the body motion detection device according to the disclosure.

The input unit 30 is formed by a keyboard 31 and a mouse 32, for example, and inputs various instructions by the user, such as a radiological technologist, to the signal processing unit 20.

The display unit 40 is formed by a liquid crystal display or a CRT display, for example, and displays a result of determination as to whether or not there is a body motion, a radiographic image of the imaged subject, etc., as necessary.

The signal processing unit 20, the input unit 30, and the display unit 40 described above can be formed by a computer system, such as a common personal computer, for example.

Next, an imaging operation to take a radiographic image is described. When a radiographic image is taken, the radiation detector 11 is placed on the imaging table 14 of the imaging apparatus 10, and the subject H is placed on the radiation detector 11. In this state, the imaging control unit 13 is operated to activate the radiation-emitting tube 12, and the radiation R transmitted through the subject H is applied to the radiation detector 11. When the imaging operation is finished, a digital image signal representing the radiographic image G0 is obtained from the radiation detector 11. The obtained radiographic image G0 can be displayed on the display unit 40.

Figure 2:
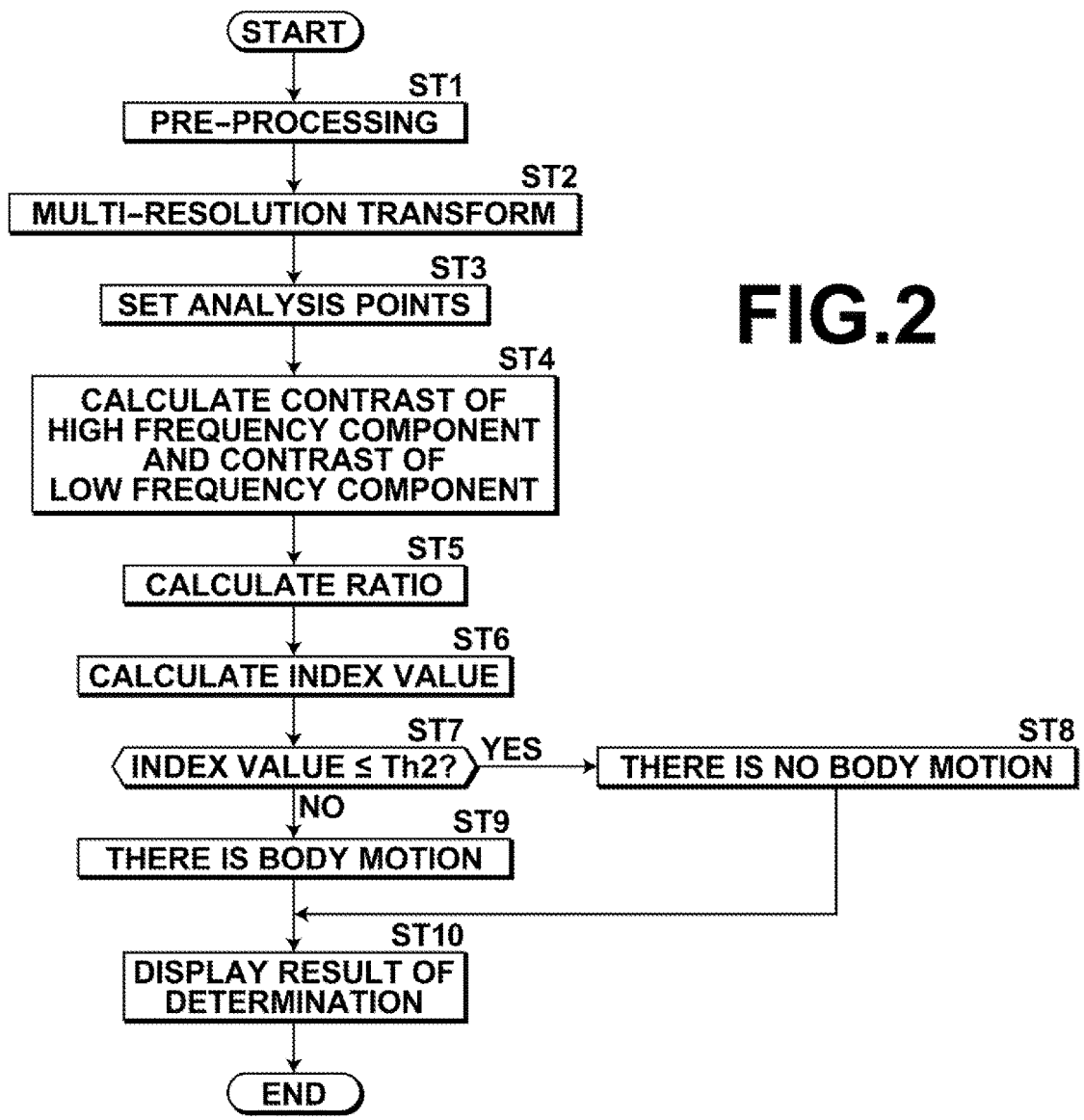
FIG. 2 is a flow chart illustrating a process carried out in the embodiment.

The radiographic image G0 is inputted to the signal processing unit 20. Now, a process performed by the signal processing unit 20 is described. FIG. 2 is a flow chart illustrating the process performed by the signal processing unit 20. First, the pre-processing unit 21 applies, to the radiographic image G0 inputted to the signal processing unit 20, correction of signal values for variation due to nonuniformity of the applied radiation, nonuniformity of detection by the radiation detector 11, etc., image processing to correct density, contrast, frequency components, etc., to improve image quality of the radiographic image G0, and other appropriate processing, as necessary (pre-processing, step ST1).

Figure 3:
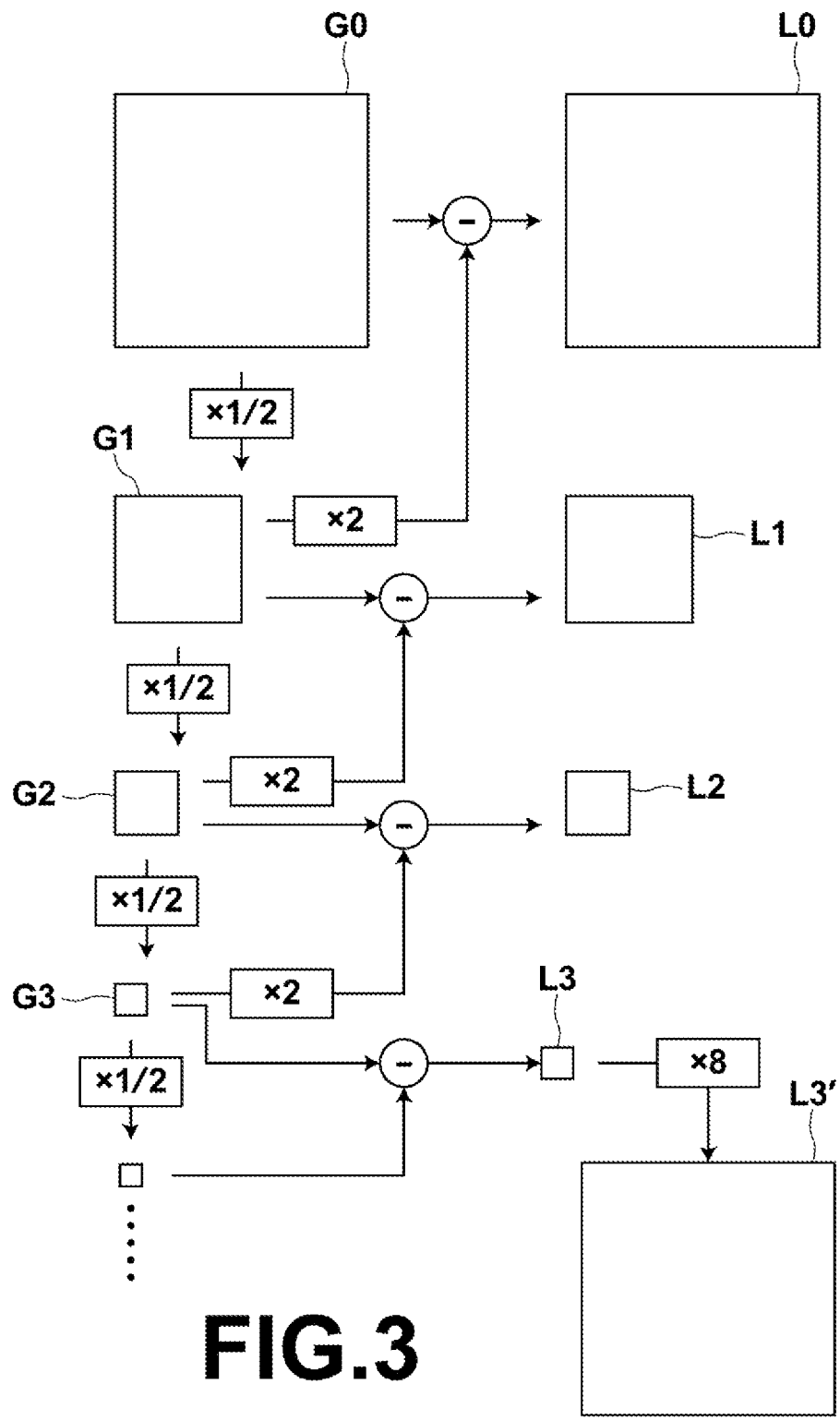
FIG. 3 is a diagram for explaining multi-resolution transform.

Then, the multi-resolution transform unit 22 applies multi-resolution transform to the pre-processed radiographic image G0, and extracts a high frequency component and a low frequency component of the radiographic image G0 (step ST2). FIG. 3 is a diagram for explaining the multi-resolution transform. First, the multi-resolution transform unit 22 filters the radiographic image G0 with a Gaussian filter with $\sigma=1$ to reduce the radiographic image G0 to ½ to generate a Gaussian component G1. The Gaussian component G1 corresponds to the radiographic image G0 reduced to ½. Then, the multi-resolution transform unit 22 performs interpolation, such as the third-order B-spline interpolation, to enlarge the Gaussian component G1 to the same size as the radiographic image G0, and subtracts the enlarged Gaussian component G1 from the radiographic image G0 to generate a Laplacian component L0 of the highest frequency band. In this embodiment, the Laplacian component L0 is used as the high frequency component. It should be noted that, in this embodiment, the highest frequency band is referred to as the 0-th frequency band, for convenience.

Then, the multi-resolution transform unit 22 filters the Gaussian component G1 with the Gaussian filter with σ=1 to further reduce the Gaussian component G1 to ½ to generate a Gaussian component G2. Then, the multi-resolution transform unit 22 enlarges the Gaussian component G2 to the same size as the Gaussian component G1, and subtracts the enlarged Gaussian component G2 from Gaussian component G1 to generate a Laplacian component L1 of the first frequency band. The above-described operations are repeated until a Laplacian component of a desired frequency band is generated, to generate Laplacian components Lj (where j=0 to n) of a plurality of frequency bands.

In this embodiment, the above-described operations are repeated until a Laplacian component L3 of the third frequency band is obtained. Then, the Laplacian component L3 is enlarged eight times to have the same size as the Laplacian component L0 of the 0-th frequency band, to generate a Laplacian component L3'. The Laplacian component L3' is used as the low frequency component.

It should be noted that the signal value of each pixel of the Gaussian component represents the density at the pixel, and the signal value of each pixel of the Laplacian component represents the magnitude of the frequency component of the frequency band at the pixel.

It should be noted that any other multi-resolution transform technique, such as the wavelet transform, may be used to generate band images of different frequency bands, and the band image of the highest frequency band may be used as the high frequency component and the band image of the third frequency band that is enlarged eight times may be used as the low frequency component similarly as described above. It should be noted that the frequency band of the low frequency component is not limited to the third frequency band, and a frequency component of any frequency band that is lower than the highest frequency band may be used as the low frequency component. Alternatively, the radiographic image G0 may be used as the high frequency component without any conversion.

Figure 4:
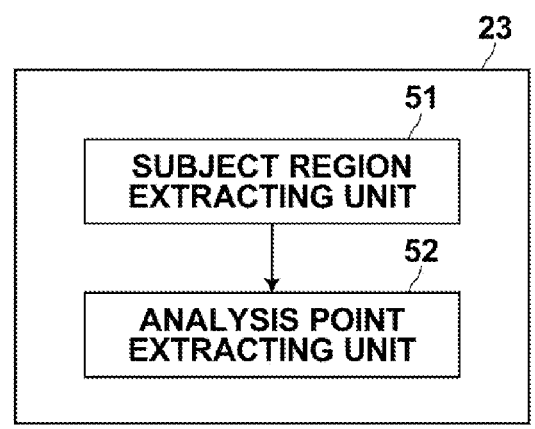
FIG. 4 is a schematic block diagram illustrating the configuration of an analysis point setting unit.

Subsequently, the analysis point setting unit 23 sets analysis points for calculating a contrast, which will be described later, on the pre-processed radiographic image G0 (step ST3). Specifically, the analysis points are set using the low frequency component L3'. Now, how the analysis points are set is described. FIG. 4 is a schematic block diagram illustrating the configuration of the analysis point setting unit 23. As shown in FIG. 4, the analysis point setting unit 23 includes a subject region extracting unit 51 and an analysis point extracting unit 52. The subject region extracting unit 51 extracts a subject region from the radiographic image G0 in order to limit an object of the body motion detection to a subject region containing bone regions in the radiographic image G0 to remove influences of a skin line and an irradiation field frame captured in the radiographic image G0. In order to determine whether or not there is a body motion of the subject during an imaging operation, it is necessary to extract high contrast regions in the radiographic image G0. To this end, the subject region extracting unit 51 in this embodiment extracts a region containing bone regions as the subject region.

Figure 5:
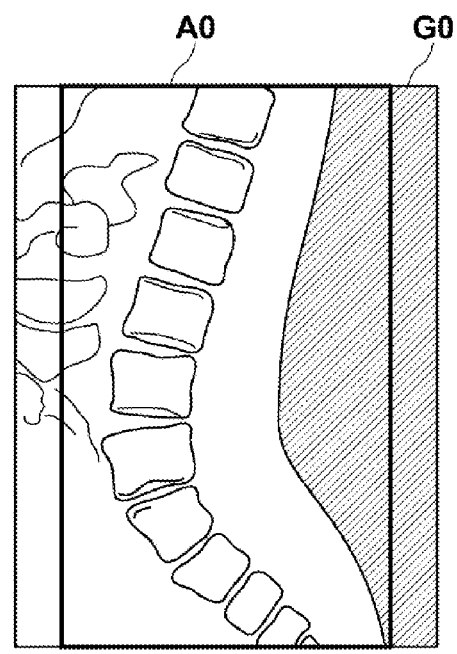
FIG. 5 is a diagram showing an example of a radiographic image.

Specifically, the subject region is extracted from the radiographic image G0 using any of various segmentation techniques, such as a technique using results of learning about the subject of interest, a rule-based technique about the subject, graph cut, etc. For example, in a case where a part of the lumbar spine is extracted from the radiographic image G0 containing the lumbar spine, as shown in FIG. 5, a region having a predetermine size containing the lumbar spine is extracted from the radiographic image G0 as a subject region A0 by using results of learning about the shape of the lumbar spine.

It should be noted that, the reason of removing the skin line as described above is that, since the skin line of the subject H differs among individuals and the sharpness of the skin line varies depending on the thickness of the subject H, it is difficult to accurately set the analysis points on the skin line, and, even if the analysis points can be set on the skin line, it is difficult to accurately determine whether or not there is a body motion. The skin line can be removed by detecting the skin line of the subject H contained in the subject region A0, and performing erosion by a few pixels on the detected skin line to reduce the peripheral region of the subject H contained in the subject region A0.

Figure 6:
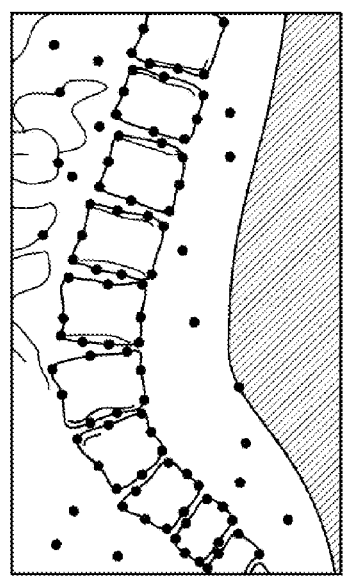
FIG. 6 is a diagram showing an example of set analysis points.

The analysis point extracting unit 52 extracts the analysis points, which serve as references for the determination as to whether or not there is a body motion, from the subject region A0. It is preferred that the analysis points are extracted from positions for which whether or not there is a body motion can easily be determined. Specifically, it is preferred to extract the analysis points along edges of the bone regions. To this end, the analysis point extracting unit 52 extracts, as the analysis points, pixels having relatively high pixel values from the subject region A0 in the low frequency component L3' generated by the multi-resolution transform unit 22. Specifically, the analysis point extracting unit 52 compares the pixel value of each pixel in the subject region A0 of the low frequency component L3' with a threshold value Th1, and extracts pixel positions where the pixel value exceeds the threshold value Th1 as the analysis points. The threshold value Th1 is calculated, for example, as Th1=σ×α, where σ is a standard deviation of pixel values in the subject region A0 of the low frequency component L3', and α is a coefficient. The coefficient α may be set as appropriate depending on the pixel values of the pixels of the low frequency component L3'. An example of the thus set analysis points is shown in FIG. 6.

Figure 7:
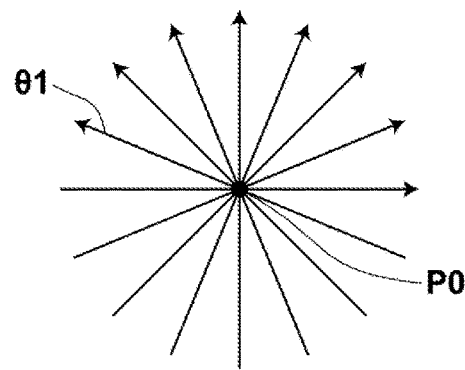
FIG. 7 is a diagram showing eight directions with an analysis point being the center.

Subsequently, the contrast calculating unit 24 calculates a contrast of the high frequency component and a contrast of the low frequency component at each analysis point (step ST4). During a short time (several tens milliseconds to several hundreds milliseconds) for which the radiation is applied to the subject, a body motion appears as blur in one direction. When a body motion occurs, degradation of the radiographic image G0 appears in the same direction as the direction of the body motion, and does not appear in a direction perpendicular to the direction of the body motion. Based on this fact, the contrast calculating unit 24 first calculates a gradient direction of the edge at each analysis point. Specifically, the contrast calculating unit 24 sets eight directions with an analysis point P0 being the center on the low frequency component L3', as shown in FIG. 7. For example, assuming that the upward direction from the bottom of the drawing is the reference (0°), eight directions corresponding to −67.5°, −45°, −22.5°, 0°, 22.5°, 45°, 67.5° and 90° are set. The eight directions are denoted by θ1 to θ8, respectively. It should be noted that the number of the directions to be set is not limited to eight, and any number of directions, such as two directions, four directions, or sixteen directions, may be set.

Then, for each direction, an analysis region of a specific size with the analysis point P0 being the center is set. The analysis region is a rectangular region of 9×9 pixels, for example. Then, a plurality of lines are virtually set in the analysis region, and a difference value between the maximum value and the minimum value of pixel values along each line is calculated as a contrast along the line. The direction of the lines is the same as the direction for which the analysis region is set. For example, in the case of an analysis region set for the direction θ1 shown in FIG. 7, the direction of the lines set in the analysis region is θ1.

Figure 8:
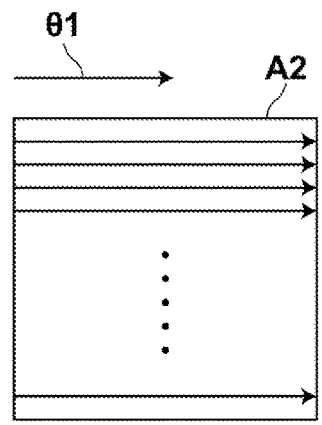
FIG. 8 is a diagram for explaining an analysis region and lines in the horizontal direction.

FIG. 8 is a diagram for explaining an analysis region and lines in the horizontal direction. As shown in FIG. 8, a plurality of lines are set in an analysis region A2, which is set for a specific direction θ1 with respect to the analysis point P0. The number of lines may be the same as the number of pixels in the vertical direction of the analysis region A2. Namely, when the size of the analysis region A2 is 9×9 pixels, the number lines may be nine. However, the number lines may be reduced by decimation, as appropriate.

Then, the contrast calculating unit 24 calculates a mean value of the contrasts of all the lines as a contrast with respect to the direction in which the analysis region is set on the low frequency component L3'. Then, the contrast calculating unit 24 calculates, for each of the analysis regions set for the eight directions θ1 to θ8, a mean value of the contrasts as a contrast CLθi (where i=1 to 8) with respect to the analysis region. Further, the contrast calculating unit 24 determines, as the gradient direction of the edge at the analysis point, a direction for which the analysis region with the highest contrast among the calculated eight contrasts CLθi is set.

Similarly, the contrast calculating unit 24 calculates eight contrasts CHθi (where i=1 to 8) of the high frequency component L0 for all the eight directions θ1 to θ8 at all the analysis points, similarly to the contrasts CHθi of the low frequency component L3'. Then, the contrast calculating unit 24 determines, as the gradient direction of the edge at the analysis point, a direction for which the analysis region with the highest contrast among the calculated eight contrasts CHθi is set.

Since the direction in which the contrast changes at each analysis point is the same for the low frequency component L3' and the high frequency component L0, the gradient directions determined for the edge at each analysis point are the same. Therefore the contrast CHθi of the high frequency component and the contrast CLθi of the low frequency component with respect to the same gradient direction of the edge at each analysis point are calculated.

When there is a body motion during an imaging operation, the contrast of the high frequency component in the obtained radiographic image G0 decreases, whereas the contrast of the low frequency component in the radiographic image G0 scarcely decreases. Further, while the contrast of the entire radiographic image varies depending on imaging conditions or the type of subject, the variation appears as a difference of the contrast of the low frequency component. Therefore, a ratio of the contrast of the high frequency component to the contrast of the low frequency component can be used as an index indicating whether or not there is a body motion.

Therefore the ratio calculating unit 25 calculates a ratio of the contrast CHθi of the high frequency component to the contrast CLθi of the low frequency component at each analysis point, specifically, a ratio CRθi (=CHθi/CLθi) of the contrast CHθi of the high frequency component to the contrast CLθi of the low frequency component (step ST5). Further, the ratio calculating unit 25 calculates, for each direction θi, a mean value CRmθi of the ratios CRθi, and calculates the lowest mean value CRmθi as an index value for determining whether or not there is a body motion (step ST6).

It should be noted that the method for calculating the index value for determining whether or not there is a body motion is not limited to the above-described method. For example, a ratio CRθi of the contrast CHθi of the high frequency component to the contrast CLθi of the low frequency component may be calculated for all the eight directions at each analysis point, a mean value CRmθi of the ratios CRθi of the contrast CHθi of the high frequency component to the contrast CLθi of the low frequency component at all the analysis points for each direction θi may be calculated, and the lowest mean value CRmL among the calculated mean values may be calculated as an index value for determining whether or not there is a body motion.

As described above, when there is a body motion during an imaging operation, the contrast of the high frequency component in the obtained radiographic image G0 decreases, whereas the contrast of the low frequency component in the radiographic image G0 scarcely decreases. Therefore, the index value is nearly 1 when there is no body motion, and the index value is smaller than 1 when there is a body motion and the value is smaller when the body motion is larger.

Then, the determining unit 26 compares the index value with a threshold value Th2 and determines whether or not the index value is equal to or greater than the threshold value Th2 (step ST7). If the index value is equal to or greater than the threshold value Th2, the determining unit 26 determines that there is no body motion (step ST8). If the index value is smaller than the threshold value Th2, the determining unit 26 determines that there is a body motion (step ST9). The threshold value Th2 is a predetermined value smaller than 1.

Figure 9:
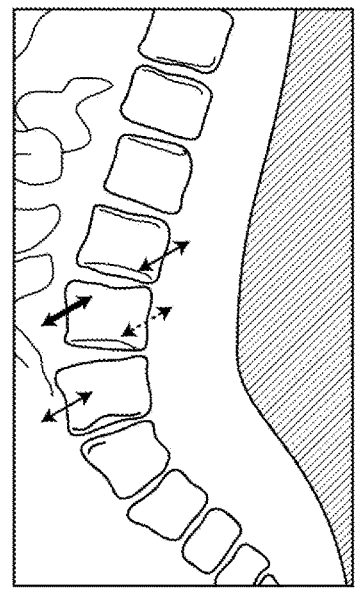
FIG. 9 is a diagram showing an example of a display screen showing a result of determination when it is determined that there is a body motion.
Figure 10:
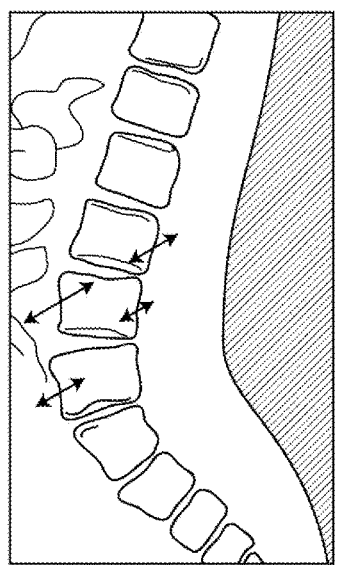
FIG. 10 is a diagram showing an example of a display screen showing a result of determination when it is determined that there is a body motion.

The display control unit 27 displays the result of determination by the determining unit 26 on the display unit 40 (step ST10), and the process ends. FIG. 9 is a diagram showing a display screen showing a result of determination when it is determined that there is a body motion. As shown in FIG. 9, on the display screen showing the result of determination, the radiographic image G0 and arrows indicating the direction and the magnitudes of the body motion are added to the analysis points. It should be noted that the number of analysis points to which the arrows are added may be a predetermined number of analysis points from the top in descending order of the ratio CRθi calculated for each analysis point (four in FIG. 9), or may be all the analysis points with the index value smaller than the threshold value Th2. The color of each arrow may be changed depending on the magnitude of the ratio CRθi, or the line type of each arrow may be changed depending on the magnitude of the ratio CRθi, as shown in FIG. 9. In this embodiment, the body motion is larger when the ratio CRθi is smaller, and each arrow indicates a larger body motion when the ratio CRθi is smaller. Alternatively, the length of each arrow may be changed depending on the magnitude of the ratio CRθi, as shown in FIG. 10. In the example shown in FIG. 10, the arrow is longer when the ratio is smaller. Displaying the result of determination in this manner facilitates seeing the position where the body motion occurs and the magnitude of the body motion on the radiographic image G0.

Figure 11:
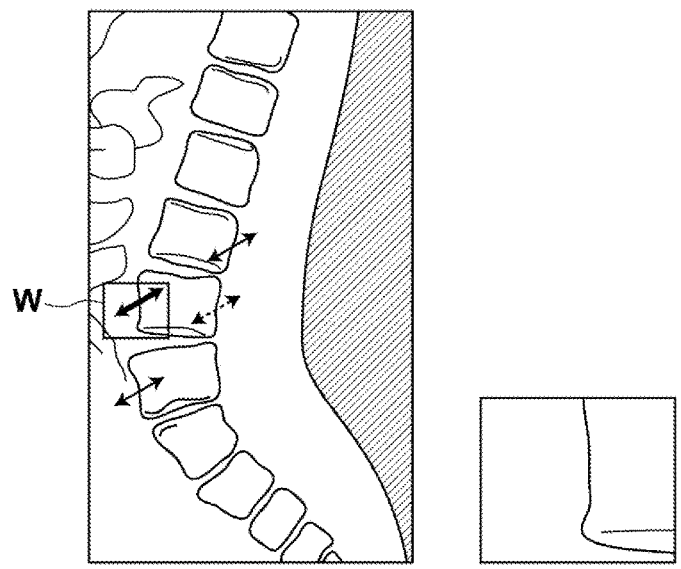
FIG. 11 is a diagram showing an example of a display screen showing a result of determination when it is determined that there is a body motion.

Even when the arrows are provided, as described above, one may wish to check the body motion by visual observation of the radiographic image G0. However, the display unit 40 provided in an imaging room for taking a radiographic image has relatively low resolution, and the observation environment is relatively bright, and it is not easy to check the body motion by visual observation. To address this problem, a function to set a region of interest W of a predetermined size on the radiographic image G0 may be provided, and an enlarged image of the region of interest W may be displayed side by side with the radiographic image G0, as shown in FIG. 11. The position of the region of interest W may be set in advance such that the region of interest contains an analysis point provided with the arrow, or the position of the region of interest W may be changed to a desired position on the radiographic image G0 by the user via the input unit 30.

Figure 12:
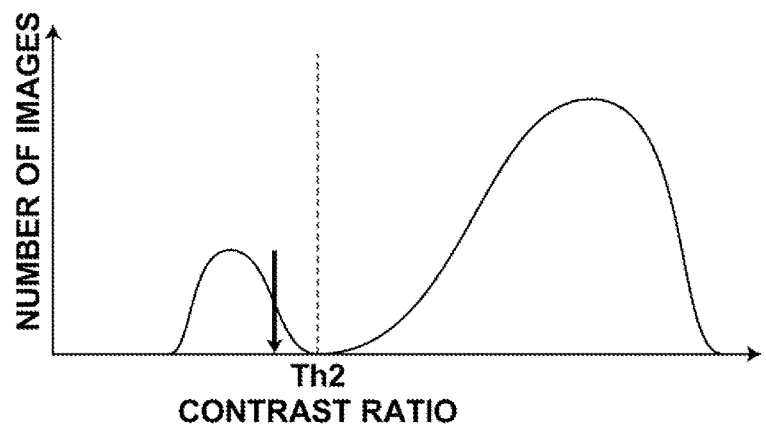
FIG. 12 shows a histogram where values of contrast ratio are plotted along the horizontal axis, and the number of images for which it is determined that there is a body motion and the number of images for which it is determined that there is no body motion for each value of the contrast ratio are plotted along the vertical axis.

Further, the index value may be displayed on the display unit 40. In this case, simply displaying numerical values may not facilitate determining the magnitude of the body motion. Results of determinations as to whether or not there is a body motion made so far may be used to facilitate understanding the magnitude of the body motion in the radiographic image G0 being analyzed. For example, as shown in FIG. 12, a histogram where values of the contrast ratio, which is the index value, are plotted along the horizontal axis, and the number of images for which it is determined that there is a body motion and the number of images for which it is determined that there is no body motion corresponding to each value of the contrast ratio are plotted along the vertical axis may be displayed, and the index value of the radiographic image G0 being analyzed may be pointed by an arrow on the histogram. It should be noted that, in FIG. 12, the range of the histogram on the left of the threshold value Th2 indicates that there is a body motion, and the range of the histogram on the right of the threshold value Th2 indicates that there is no body motion.

On the other hand, when it is determined that there is no body motion, a message "There is no body motion" may be displayed, or a sound may be outputted, for example. Also, when it is determined that there is a body motion, a message "There is a body motion. Please perform imaging again." may be displayed, or a sound may be outputted, for example.

As described above, in this embodiment, whether or not there is a body motion of the subject contained in the radiographic image G0 is determined based on the ratio of the contrast of the high frequency component to the contrast of the low frequency component of the radiographic image G0. When there is a body motion during an imaging operation, the contrast of the high frequency component in the obtained radiographic image G0 decreases, whereas the contrast of the low frequency component in the radiographic image G0 scarcely decreases. Further, while the contrast of the entire radiographic image varies depending on imaging conditions or the type of subject, the variation appears as a difference of the contrast of the low frequency component. Therefore, the ratio of the contrast of the high frequency component to the contrast of the low frequency component can be used as an index indicating whether or not there is a body motion. In this embodiment, whether or not there is a body motion is determined using the contrast of the high frequency component and the contrast of the low frequency component, which are independent from the imaging conditions or the type of subject, and not using results of learning as in the technique taught in Patent Literature 1, for example. This allows stable determination as to whether or not there is a body motion without being influenced by the imaging conditions or the type of subject.

In some cases, the subject H may include an artificial object, such as a metal forming an artificial joint. Also, the radiographic image G0 may contain an artificial object such as a lead protector when a lead protector is used during an imaging operation to protect the reproductive organs, or the like. Further, the digestive organs, such as the stomach and intestines, of the subject H may include gas such as air. The artificial object appears in the radiographic image G0 as a high-luminance region, and gas appears in the radiographic image G0 as a low luminance region. The shapes of such regions and the presence or absence of these regions in the subject H vary among individuals, similarly to the skin line of the subject H. Further, sharpness of edges of these regions is not so high, and it is difficult to accurately set the analysis points in these regions. Even if the analysis points are set in these regions, it is difficult to accurately determine whether or not there is a body motion based on the ratio of the contrast of the high frequency component to the contrast of the low frequency component. For this reason, the analysis point setting unit 23 may set the analysis points in regions other than an inappropriate region, such as a region of an artificial object or gas, which is inappropriate for the determination as to whether or not there is a body motion. The configuration of the analysis point setting unit in this case is shown in FIG. 13.

Figure 13:
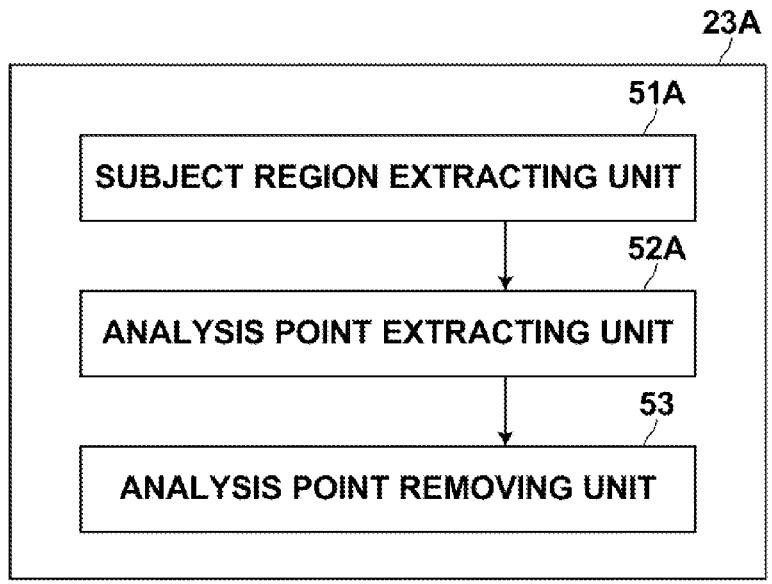
FIG. 13 is a schematic block diagram illustrating another configuration of the analysis point setting unit.

As shown in FIG. 13, the analysis point setting unit 23A includes a subject region extracting unit 51A, an analysis point extracting unit 52A, and an analysis point removing unit 53. It should be noted that the configurations of the subject region extracting unit 51A and the analysis point extracting unit 52A are the same as those of the subject region extracting unit 51 and the analysis point extracting unit 52, and detailed descriptions thereof are omitted. The analysis point removing unit 53 removes an analysis point in an inappropriate region, which is inappropriate for the determination as to whether or not there is a body motion, from the analysis points extracted by the analysis point extracting unit 52A.

The artificial object appears in the radiographic image G0 as a region having higher luminance than regions of structures, such as bones, of the human body. The gas appears in the radiographic image G0 as a region having lower luminance than regions of structures of the human body. Based on this fact, the analysis point removing unit 53 generates a histogram of luminance values of the subject region A0, and extracts a region having a luminance higher than a first threshold value in the histogram as an artificial object region. Also, the analysis point removing unit 53 extracts a region having a luminance lower than a second threshold value (<first threshold value) as a gas region. Then, the analysis point removing unit 53 sets the extracted artificial object region and gas region as inappropriate regions which are inappropriate for the determination as to whether or not there is a body motion, and removes the analysis points in the inappropriate regions from the analysis points extracted by the analysis point extracting unit 52A. It should be noted that the first and second threshold values are set such that luminance values of structures of the human body are included between the threshold values.

It is preferred that the analysis points be set in regions of structures, such as bones, of the human body. To this end, machine learning of features of the structures of the human body, such as bones, included in the human body may be performed, and a region which does not have the features of the structures of the human body may be set as the inappropriate region based on the results of the learning.

Alternatively, since the artificial object region in the subject region A0 has a higher contrast than those of the structures of the human body, a region having a high contrast in the subject region A0 may be set as the inappropriate region. It should be noted that, if a part of the imaging apparatus 10 is captured in the radiographic image G0, the region has a high contrast. In this case, however, the high contrast region dose not move when the subject H moves. It is therefore preferred that a region having a particularly high contrast be excluded from regions in which the analysis points are set for determining whether or not there is a body motion.

In a case where a thoracicoabdominal part is imaged, the digestive organs contained in the image tend to include many gas regions. On the other hand, in a case where any of the limbs is imaged, no gas region is included. In a case where a radiographic image is taken at an orthopedic hospital for diagnosis, it is often the case that an artificial object, such as a metal, is contained in the image. It is therefore preferred that the type of the inappropriate region be changeable to set a different type of inappropriate region depending on the imaged body part and/or the purpose of diagnosis. This allows quickly and accurately setting the inappropriate region.

While the analysis points in the inappropriate region are removed after the analysis points are extract in the above description, the inappropriate region may be first extracted and removed from the subject region A0, and then the analysis points may be extracted from the subject region A0 from which the inappropriate region has been removed.

The body motion includes those due to movement of the subject H as a whole, and those due to a local movement of the subject H, such as movement of the lung field and the diaphragm along with respiration, and heart beats. Further, the local movement and the other type of movement have different statistic values or different statistic distributions of the index values for determining whether or not there is a body motion, which are calculated as described above. Therefore the determining unit 26 may perform statistic processing on the index values, and may determine whether or not there is a local body motion based on the result of the statistic processing.

When there is a body motion at only a part of the radiographic image G0, only the part has a small index value for determining whether or not there is a body motion. Then, when an average value of the index values is calculated only for analysis points with the index values within a specific range of the entire index value distribution (for example, a range of 30% from the smallest) among the plurality of analysis points, the average value when there is a body motion at the analysis points is smaller than the average value when there is no body motion at the analysis points. Therefore the ratio calculating unit 25 may calculate an average value of the index values of analysis points with the index values within a specific range (for example, a range of 30% from the smallest) in the entire index value distribution, and the determining unit 26 may determine there is a body motion in a local region where the analysis points are present if the average value is smaller than a predetermined threshold value.

Figure 14:
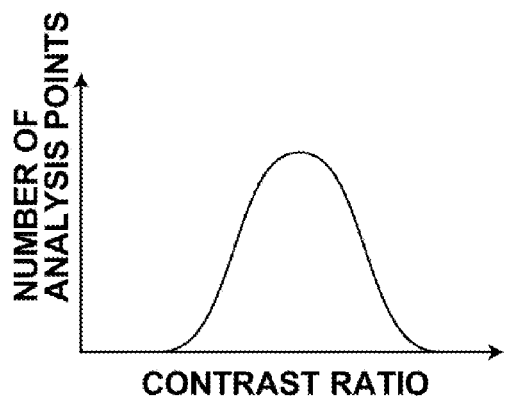
FIG. 14 shows a histogram which plots index values along the horizontal axis, and the numbers of analysis points along the vertical axis.
Figure 15:
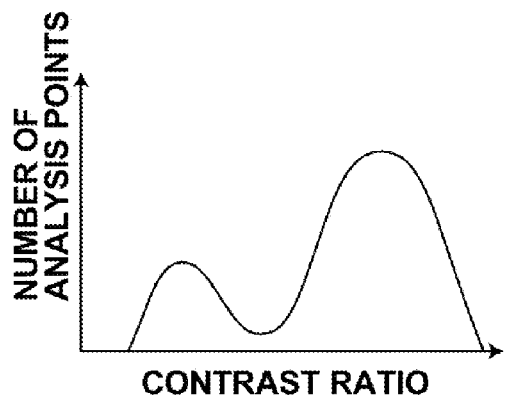
FIG. 15 shows another histogram which plots index values along the horizontal axis, and the numbers of analysis points along the vertical axis.

When there is a body motion of the entire subject H in one direction, or there is no body motion, a histogram (which will hereinafter be referred to as "histogram of index values") which plots the index values along the horizontal axis and the numbers of analysis points having the individual index values along the vertical axis shows a single-peak distribution, as shown in FIG. 14. On the other hand, a local body motion tends to be larger than a body motion of the entire subject H, and the histogram of index values shows a peak at lower index values. When there is a local body motion, the histogram shows a mixture distribution with two peaks, as shown in FIG. 15. Therefore, the determining unit 26 may generate the histogram of index values, and, when the histogram of index values shows a mixture distribution rather than a single-peak distribution, the determining unit 26 may determine that there is a local body motion. It should be noted that a mixture distribution can be separated using a known technique, such as separating the distribution at a portion having the lowest frequency. By separating the histogram of contrast and identifying the analysis points having the index values forming the peak at the lower index values, it can be determined that there is a body motion at the local position where the identified analysis points are present.

In a case where the thoracicoabdominal part is imaged, the lung field, the ribs, and the heart may move due to respiration and heart beats, and the taken image often includes a local body motion. On the other hand, in a case where any of the limbs is imaged, the entire limb moves when there is a body motion, and often no local body motion is included in the taken image. Since there are cases where a local body motion may occur and may not likely occur depending on the imaged body part, the determining unit 26 may determine, depending on the imaged body part, whether or not to perform the determination as to whether or not there is a local body motion by performing the statistic processing on the index values.

Although the analysis points for determining whether or not there is a body motion are set by the analysis point setting unit 23 in the above-described embodiment, the analysis points may be set manually by the user on the radiographic image G0 displayed on the display unit 40. Alternatively, the analysis points may be at fixed positions on the radiographic image G0. At this time, it is preferred to remove the inappropriate region from the radiographic image G0 before performing the determine as to whether or not there is a body motion, so that no analysis point is set in the inappropriate region.

Further, although the multi-resolution transform unit 22 obtains the high frequency component and the low frequency component of the radiographic image G0 by applying multi-resolution transform to the radiographic image G0 in the above-described embodiment, Fourier transform may be applied to an area of a predetermined range which contains an analysis point of the radiographic image G0 to obtain a power spectrum with respect to the analysis point, and a value of a predetermined high frequency band and a value of a predetermined low frequency band in the power spectrum may be calculated as the contrast of the high frequency component and the contrast of the low frequency component at the analysis point. In this case, the ratio of the contrast of the high frequency component to the contrast of the low frequency component is substantially the ratio of the high frequency component to the low frequency component in the power spectrum.

Further, although whether or not there is a body motion is determined in the above-described embodiment using a radiographic image obtained by the imaging apparatus 10 that takes a radiographic image of a subject using a radiation detector 11, the disclosure is also applicable to a case where radiographic image information of a subject is recorded on a storage phosphor sheet serving as a radiation detector material, as taught in Japanese Unexamined Patent Publication Nos. 8(1996)-266529 and 9(1997)-024039, for example, and whether or not there is a body motion is determined by using a radiographic image obtained by photoelectrically reading the image from the storage phosphor sheet.

What is the claimed is:

1. A body motion detection device comprising: a processor that: calculates a contrast of a high frequency component and a contrast of a low frequency component of a radiographic image at each of a plurality of analysis points contained in the radiographic image, the analysis points being set for calculation of the contrast of the high frequency component and the contrast of the low frequency component, wherein processor generates, from the radiographic image, a high frequency image containing the high frequency component and a low frequency image containing the low frequency component, determines, at each analysis point on each of the high frequency image and the low frequency image, a gradient direction of an edge portion contained in an analysis region with the analysis point being the center, and calculates a contrast along the gradient direction of each of the high frequency image and the low frequency image as the contrast of the high frequency component and the contrast of the low frequency component;

calculates a ratio of the contrast of the high frequency component to the contrast of the low frequency component for the gradient direction determined at each of the analysis points; and determines a smallest ratio among ratios calculated for the gradient directions as an index value indicating a body motion, and determining whether or not there is a body motion of a subject contained in the radiographic image based on a result of statistical processing of the index values at the analysis points.

2. The body motion detection device as claimed in claim 1, wherein the processor determines whether or not there is a body motion at analysis points with an index values within a specific range of an entire index value distribution from a smallest based on a statistic value of the index values at the analysis points with the index values within the specific range of the entire index value distribution from the smallest.

3. The body motion detection device as claimed in claim 2, wherein the processor generates a distribution of all the index values, and determines whether or not there is a body motion based on the distribution.

4. The body motion detection device as claimed in claim 1, wherein the processor determines, depending on a body part of the subject, whether or not to perform the determination as to whether or not there is a body motion based on the result of the statistical processing.

5. The body motion detection device as claimed in claim 1, wherein the processor further sets the analysis point on the radiographic image.

6. The body motion detection device as claimed in claim 5, wherein the processor extracts a region of the subject from the radiographic image, and extracts a point at which the low frequency component in the region exceeds a specific threshold value as the analysis point.

7. The body motion detection device as claimed in claim 5, wherein the processor sets the analysis points in a region other than an inappropriate region which is inappropriate for the determination as to whether or not there is a body motion.

8. The body motion detection device as claimed in claim 7, wherein the inappropriate region is at least one of an artificial object, gas, and a peripheral region of the subject contained in the radiographic image.

9. The body motion detection device as claimed in claim 7, wherein the processor sets the inappropriate region depending on a body part of the subject and/or a purpose of diagnosis.

10. The body motion detection device as claimed in claim 1, wherein the processor further displays a result of the determination as to whether or not there is a body motion on a display device.

11. The body motion detection device as claimed in claim 10, wherein the processor displays the radiographic image wherein information indicating a magnitude of the index value at each analysis point is added to the analysis point.

12. A body motion detection method comprising: calculating a contrast of a high frequency component and a contrast of a low frequency component of a radiographic image at each of a plurality of analysis points contained in the radiographic image, the analysis points being set for calculation of the contrast of the high frequency component and the contrast of the low frequency component, wherein the contrast of the high frequency component and the contrast of the low frequency component are calculated by generating, from the radiographic image, a high frequency image containing the high frequency component and a low frequency image containing the low frequency component, determining, at each analysis point on each of the high frequency image and the low frequency image, a gradient direction of an edge portion contained in an analysis region with the analysis point being the center, and calculating a contrast along the gradient direction of each of the high frequency image and the low frequency image as the contrast of the high frequency component and the contrast of the low frequency component; calculating a ratio of the contrast of the high frequency component to the contrast of the low frequency component for the gradient direction determined at each of the analysis points; and determining a smallest ratio among ratios calculated for the gradient directions as an index value indicating a body motion, and determining whether or not there is a body motion of a subject contained in the radiographic image based on a result of statistical processing of the index values at the analysis points.

* * * * *